(12) United States Patent
Kyriakis (10) Patent No.: US 9,528,821 B2
(45) Date of Patent: Dec. 27, 2016

(54) HIGH SPEED MAGNETIC OSCILLATING DEVICE

(71) Applicant: Proton Products International Limited, Beaconsfield, Buckinghamshire (GB)

(72) Inventor: John Kyriakis, Beaconsfield (GB)

(73) Assignee: BAE Systems plc, London (GB)

( * ) Notice: Subject to any disclaimer, the term of this patent is extended or adjusted under 35 U.S.C. 154(b) by 16 days.

(21) Appl. No.: 14/607,437

(22) Filed: Jan. 28, 2015

(65) Prior Publication Data

US 2015/0211982 A1    Jul. 30, 2015

(30) Foreign Application Priority Data

Jan. 30, 2014 (GB) .................................. 1401564.8
Feb. 20, 2014 (GB) .................................. 1402987.0

(51) Int. Cl.

| | |
|---|---|
| *G01B 11/24* | (2006.01) |
| *G01N 21/952* | (2006.01) |
| *G02B 26/10* | (2006.01) |
| *G01B 11/10* | (2006.01) |

(52) U.S. Cl.
CPC ......... *G01B 11/2433* (2013.01); *G01B 11/105* (2013.01); *G01N 21/952* (2013.01); *G02B 26/105* (2013.01); *G01B 2210/46* (2013.01)

(58) Field of Classification Search
CPC .............. G01B 11/105; G01B 11/2433; G01B 2210/46; G01N 21/952; G02B 26/105
See application file for complete search history.

(56) References Cited

U.S. PATENT DOCUMENTS

| | | | | |
|---|---|---|---|---|
| 4,389,101 A | * | 6/1983 | van Rosmalen | G11B 7/0925 359/225.1 |
| 4,958,894 A | * | 9/1990 | Khowles | G02B 26/08 318/129 |
| 5,088,827 A | * | 2/1992 | Kyriakis | G01B 11/024 250/559.07 |
| 5,097,355 A | * | 3/1992 | Eden | H02K 33/16 359/199.1 |
| 5,099,352 A | | 3/1992 | Yamamoto | |
| 5,610,752 A | | 3/1997 | Hayakawa | |
| 5,621,529 A | | 4/1997 | Gordon | |
| 5,982,521 A | * | 11/1999 | Bessho | G02B 26/105 347/260 |
| 9,128,190 B1 | * | 9/2015 | Ulrich | G01S 17/936 |

(Continued)

FOREIGN PATENT DOCUMENTS

WO    2014097683 A1    6/2014

OTHER PUBLICATIONS

GB Search Report dated Aug. 29, 2014 of Patent Application No. GB1402987.0 filed Feb. 20, 2014.

*Primary Examiner* — Gordon J Stock, Jr.
(74) *Attorney, Agent, or Firm* — Maine Cernota & Rardin (57) ABSTRACT

A high speed oscillating system for non-contact optical scanning of an elongated product moving in a linear production process to determine the dimensional properties and surface profile integrity thereof. The system is designed to increase the scanning frequency and thereby the capability to measure the diameter or size of the product as well as its surface integrity and pick out flaws in the structure of the product in a manner which otherwise is not possible with present day systems on the market.

6 Claims, 7 Drawing Sheets

(56) References Cited

U.S. PATENT DOCUMENTS

| | | |
|---|---|---|
| 2004/0021924 A1 | 2/2004 | Yasuda |
| 2004/0085617 A1 | 5/2004 | Helsel |
| 2005/0253055 A1 | 11/2005 | Sprague |
| 2007/0127146 A1 | 6/2007 | Moon |
| 2008/0001690 A1* | 1/2008 | Yang .................... G02B 26/085 335/213 |
| 2009/0039715 A1* | 2/2009 | Noguchi ............... G02B 26/085 310/36 |
| 2009/0039716 A1* | 2/2009 | Ogawa ................. G02B 26/085 310/36 |
| 2009/0284817 A1 | 11/2009 | Orcutt |
| 2013/0301099 A1* | 11/2013 | Mizoguchi ........... G02B 26/085 359/221.2 |
| 2015/0293349 A1* | 10/2015 | Matozaki ............... G02B 27/01 359/198.1 |

* cited by examiner

HIGH SPEED MAGNETIC OSCILLATING DEVICE

RELATED APPLICATIONS

This application claims the benefit of GB patent applications GB1401564.8, filed Jan. 30, 2014 and GB1402987.0, filed Feb. 20, 2014. Each of these applications is herein incorporated by reference in their entirety for all purposes.

FIELD OF THE INVENTION

The present invention relates to a high speed oscillating system for non-contact optical scanning of elongated products moving in a linear production process to determine the dimensional properties and surface profile integrity thereof.

BACKGROUND OF THE INVENTION

Existing industrial products, such as wires, cable, tubes, ropes and similarly elongated products which are manufactured in continuous linear processes, are preferred to be measured by non-contact methods, to determine the overall size as well as the surface integrity of the profile of the product.

These measurements usually take place while the products are being manufactured, such as during extrusion, in the case of plastic cables, tubes etc., or drawing, in the case of wires, metallic tubes and the like. Measurements at the point of manufacture are necessary, firstly to ensure compliance to specification requirements, and secondly to check on the surface integrity of the finished product.

The primary measurement applied to linearly manufactured elongated products is the diameter or size of the product, and this is done preferably by optical non-contact devices. Quality control, or surface integrity of the product, is performed in a similar manner by an optical device, whereby the profile of the product is examined to ensure that there are no faults or damage, such as ridges, valleys and the like, in the surface of the product.

In the prior art in existence at the time when the present invention was envisioned, two alternative optical systems existed, one for dimensional measurements of the product and an alternative system for checking the surface integrity of the product. These prior art systems will be explained later in this text. Both types of prior art systems, however, suffered from low maximum scanning frequencies that hinder the ultimate resolution with which they are able to detect defects and provide measurements due to the nature of their design. This has become especially troublesome in modern manufacturing lines which run at very high speeds, with such speeds only increasing each year.

What is needed, therefore, are techniques to increase the scanning frequency of optical dimensional measuring devices suitable for measuring the diameter or size of a moving product while simultaneously verifying the surface integrity of the product, during the manufacturing process of the product which can provide adequate resolution on modern, high-speed, production lines.

SUMMARY OF THE INVENTION

One embodiment of the present invention provides an apparatus for high frequency scanning of a product being manufactured in a continuous linear process comprising two high frequency generators for providing output frequencies of equal magnitude but of opposing phase; a magnetic foil with a mirrored face mounted for oscillation on a torsion axis; a light source for projecting a ray of light from the source onto the foil; a pair of induction coils operatively associated with the generators configured to generate electromagnetic forces of opposite polarity under the influence of the generators to oscillate the foil and direct successive curtains of parallel rays across the product in its linear path of travel to scan the product at the frequency of the generators; detector means for receiving the resulting format of the parallel rays of light on the other side of the product after the passage of the product, there through; and analysis means for analyzing the format of the resulting light rays light and configured to provide dimensional measurements and to verify the surface integrity of the product.

Another embodiment of the present invention provides such an apparatus wherein the high frequency generators with their associated induction coils produce an electromagnetic force (EMF) which is directed onto the magnetic foil with a mirrored face, whereby the action of the EMF on the magnetic foil, causes the magnetic foil to oscillate about its torsion axis, at the same frequency of the high frequency generators.

Still another embodiment of the present invention provides such an apparatus wherein one of the high frequency generators and associated induction coil, provide the main electronic driving force, to cause the oscillation of the, mirrored foil.

Still yet another embodiment of the present invention provides such an apparatus wherein the other of the two high frequency generators and associated induction coil, provides an opposing electromagnetic force to the driving force, in order to stabilize the oscillation of the mirrored foil and control the angular extent of the rocking motion of the foil.

A still yet further embodiment of the present invention provides such an apparatus wherein the source of light is provided by a laser or light emitting diode which directs a ray on to the mirrored face of the oscillating magnetic foil, thereby to create a series of consecutive rays, and further comprising a first lens for receiving the consecutive rays to produce a curtain of parallel rays to be scanned across the product from one side thereof and a second lens for focusing the rays after being intercepted by the moving product system for analysis by the analysis means to determine the dimensional properties and surface integrity of the product.

One embodiment of the present invention provides an apparatus for high frequency scanning of a moving product being manufactured in a continuous linear process configured to determine its dimensional proportion and surface integrity comprising two high frequency generators with two associated induction coils; a magnetic foil with a mirrored face suspended on a torsion axis to permit oscillating motion thereof; a source producing a ray of light directed onto the foil; means for oscillating the magnetic foil under the influence of electromagnetic forces of opposite polarity applied thereto from the induction coils to provide successive curtains of parallel rays of light through which the product passes in its path of travel; means for receiving the resulting format of the curtain of parallel rays after modification of its format by passage of the product there through; means of analyzing the modified format in order to locate and detect surface faults such as ridges, valleys and bare patches in the profile contour of the product; and means for measuring and individually itemizing the faults in order to ensure the suitability of the product for its subsequent application.

One embodiment of the present invention provides a device for use in an optical scanner comprising a pair of generators for providing output frequencies of equal magnitude but in opposing phase; a magnetic foil mounted for oscillation on a torsion axis; and a pair of induction coils operatively associated with the generators configured to generate electromagnetic forces of opposite polarity under the influence of the generators directed onto the foil to oscillate the foil.

Another embodiment of the present invention provides such a device wherein the foil is mirrored.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

Notation: meters per minute=m/min
meters per second=m/sec
millimeters per second=mm/sec
cycles per second=cycles/sec
scans per second=scans/sec Preferred embodiments of the invention are shown in FIGS. 1-7.

During the following discussion, reference will be made to FIGS. 1-7 and when similar items of the apparatus are used, they will be referred to with identical reference numbers.

Figure 1:
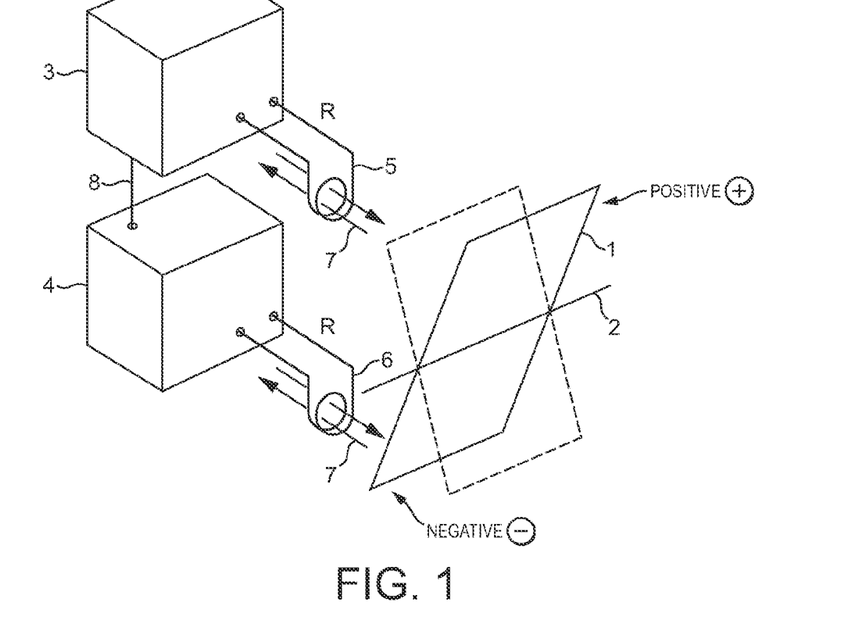
FIG. 1 is a top, front, right-side perspective view of elements of the present disclosure configured in accordance with embodiments of the present invention.

With reference to FIG. 1, a high frequency oscillating system is illustrated, comprising a foil 1, magnetized in a plus (+) and minus (−) manner, being supported by a torsion axis 2 and preferably two high frequency generators 3 and 4. Each of generators 3, 4 chains may be connected to induction coils 5, 6 respectively, thereby creating an EMF (electromagnetic force), 7 which engulfs the magnetic foil 1, whereby coil 5 is directed to the positive half of the foil 1 and coil 6 is directed to the negative half of the coil 1.

Figure 2:
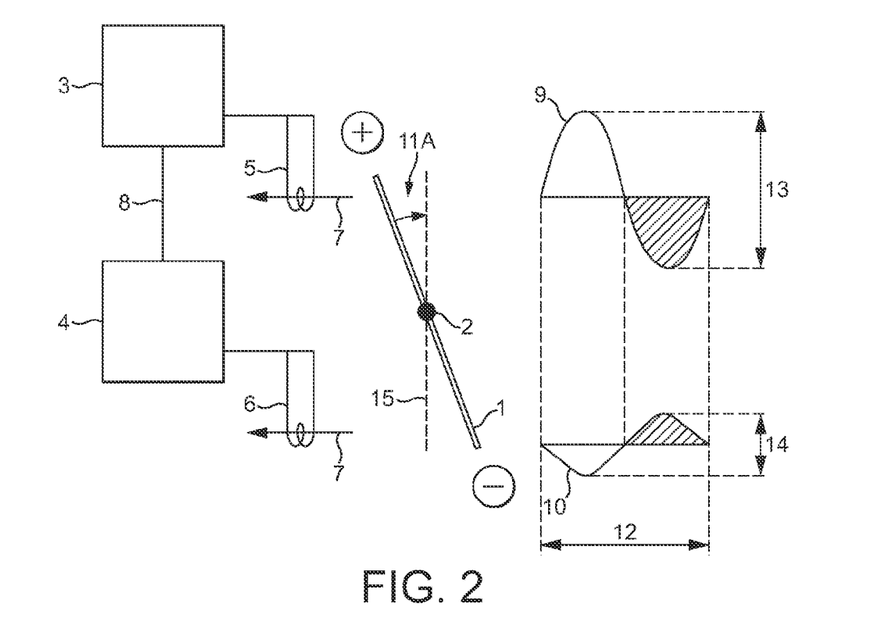
FIG. 2 is a right-side elevation view of the embodiment of the present invention shown in FIG. 1 in a first state.

In embodiments, the generators 3 and 4 are synchronized by connection 8 in such a manner whereby the output frequencies of the generators 3, 4 are identical, but in opposing phase (see FIG. 2).

FIG. 2 shows a side view of FIG. 1 wherein coils 5 and 6 are in close proximity to each half of the foil 1, in order that coil 5 acts on the positive half of the foil 1 and coil 6 acts on the negative half of the foil 1.

The EMF 7 of coil 5 has a waveform 9 shown in FIG. 2, which is the main force, driving the oscillation of foil 1, while EMF 7 of coil 6, with waveform 10 provides an opposing control force (negative feedback) to the oscillation of foil 1. The action of waveform 10, firstly secures stability of foil 1 oscillation and secondly controls the angular swing motion 11 (A+B) of the foil 1.

As previously mentioned, the waveforms 9 and 10 are synchronized to the same frequency 12 however the amplitude 13 of waveform 9 is greater than amplitude 14 of waveform 10.

The oscillation of foil 1 occurs as follows; when waveform 9 is in the negative (shaded) half of its cycle, it attracts the positive side of foil 1, from the neutral position 15 (shown dotted) through angle 11A, while waveform 10, being in the positive (shaded) half of its cycle also attracts the negative side of foil 1, thus providing the necessary opposing control as required.

Figure 3:
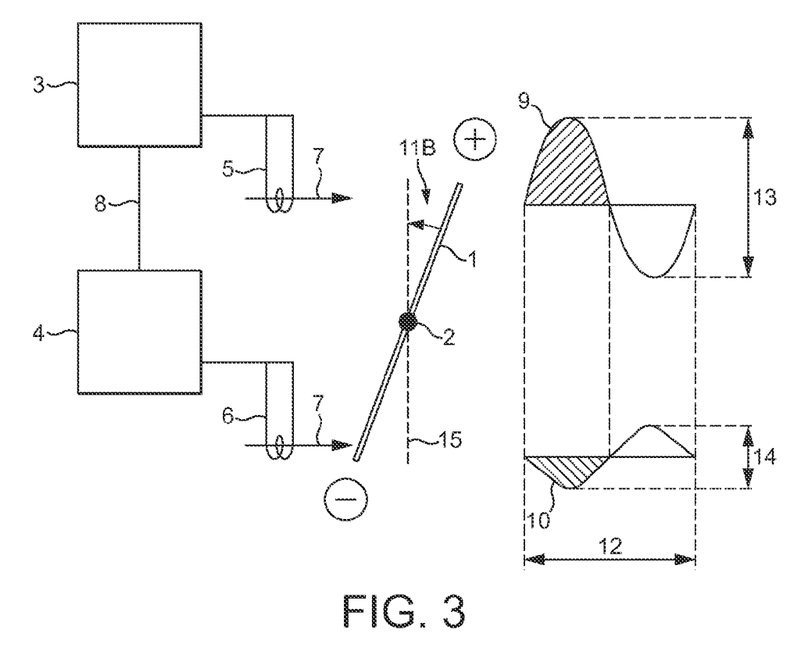
FIG. 3 is a right-side elevation view of the embodiment of the present invention shown in FIG. 1 in a second state.

FIG. 3 illustrates the position of foil 1, when waveform 9 is in its positive (shaded) half of its cycle, whereby it repels the positive half of foil 1 through angle 11B, while waveform 10 being in its negative (shaded) half, also repels the negative half of foil 1, again providing the necessary control as required. The torsion axis 2 applies an opposing resistance to the movements of foil 1 which waveform 9 has to overcome in order to produce the required swing motion.

Figure 4A:
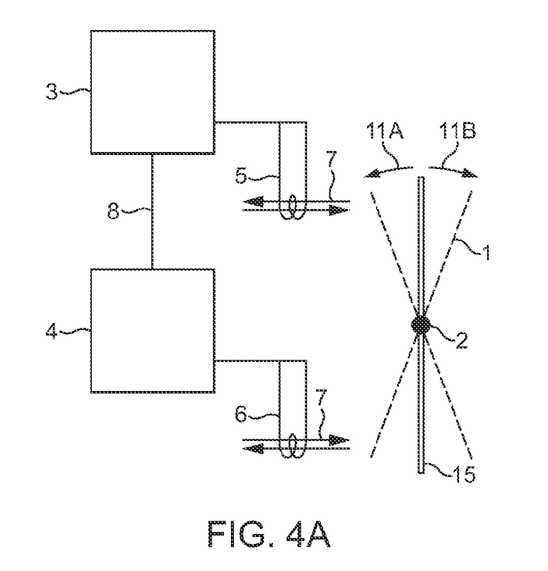
FIG. 4A is a right-side elevation view of an embodiment of the present invention.

FIG. 4A shows the angle of total angular swing of the magnetic foil oscillation of the foil 1, on its axis 2, which is 11 (A+B).

When the system is not in operation the torsion axis 2 returns foil 1 to the rest position 15.

Figure 4B:
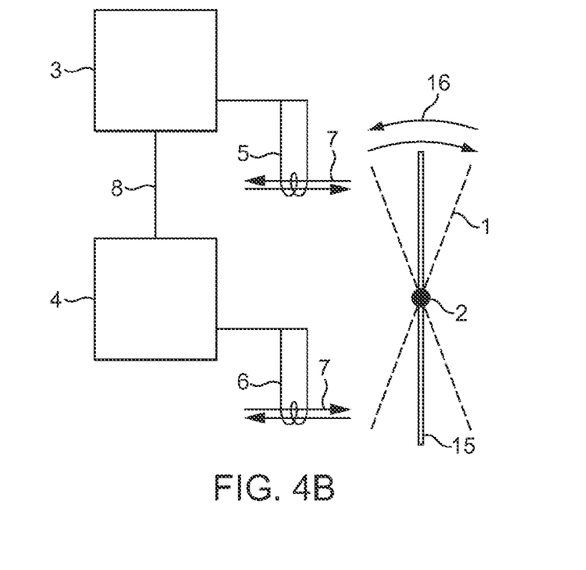
FIG. 4B is a right-side elevation view of an embodiment of the present invention.

FIG. 4B illustrates generators 3 and 4 in operation, whereby the action of coils 5 and 6 on foil 1, will cause the foil 1 to oscillate "to and fro" as at 16 on its axis 2, through an angular swing 11 (A+B) at the same frequency 12 of the generators 3, 4.

As foil 1 oscillates in a "to and fro" motion, this equates to 2 scans per one single cycle of frequency 12. This is a very useful advantage, as it doubles the frequency of generators 3 and 4. The oscillation frequency 12 that may be achieved using this principle may be approximately 20,000 cycles/second, which equates to 40,000 scans/sec of foil 1, thus providing a considerable advantage in industrial applications for dimensional measurement of products, as well as measurement of their surface integrity.

Figure 5:
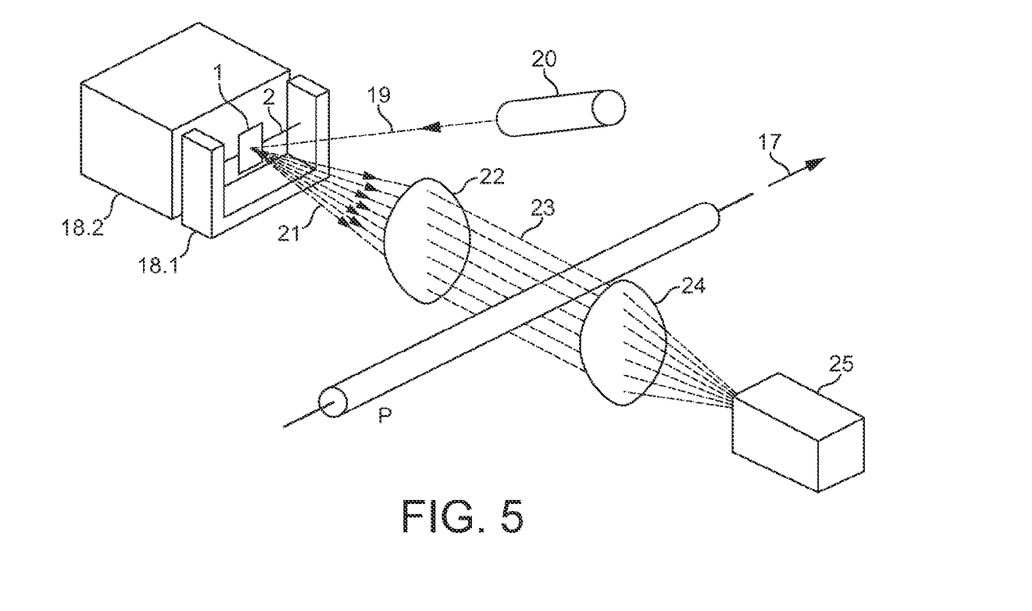
FIG. 5 is a top, front, right-side perspective view of an embodiment of the present invention applied to the measurement of dimensions as well as surface imperfections in an extruded product.

FIG. 5 shows the system of the invention used in an industrial application whereby a product, such as an electric cable, wire, plastic tube, hose or the like, is progressing in a linear path of travel 17 during its manufacturing process (not shown). The system shown comprises a magnetic foil 1 with a mirrored face, which is supported by a torsion axis 2, in a cradle 18.1 and two high frequency generators 3 and 4 (not shown) with associated induction coils 5, 6 (not shown) in housing 18.2.

A ray of light 19 from a source 20, such as, laser LED (light emitting diode), is directed on to the mirrored face of foil 1, and by the action of the oscillating foil 1, a series of consecutive rays 21 are produced. The rays 21 are directed on to a lens 22 which convert the rays 21 into a sheet or curtain of parallel scanning rays 23, crossing the product P from one side thereof in its path of travel 17.

A lens 24 positioned on the other side of product P receives rays 23 after passing therethrough and focuses the rays 23 on to a unit 25, which analyses the focused rays 23, to provide dimensional as well as surface integrity properties of the product 16.

Figure 6:
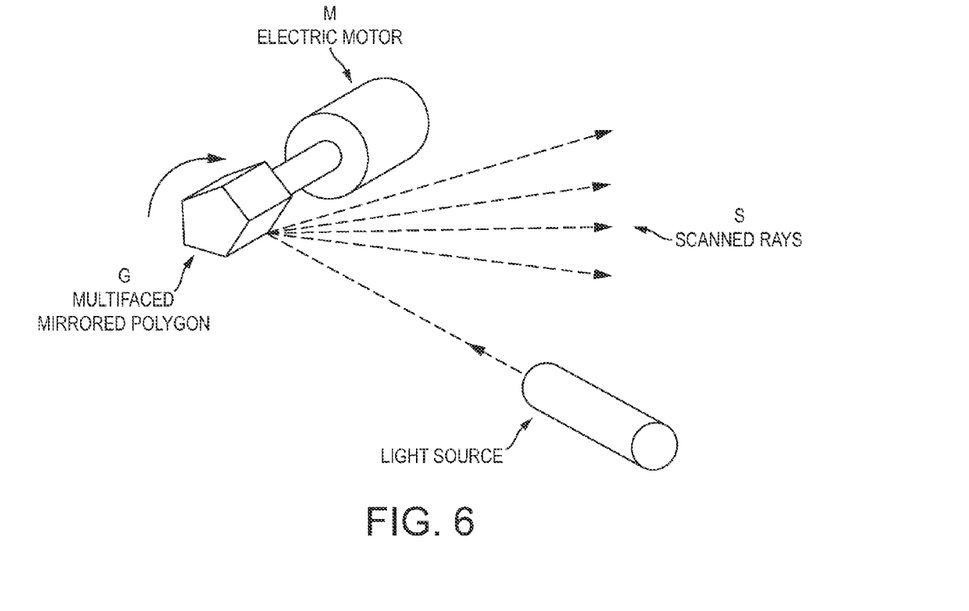
FIG. 6 is a top, front, left-side perspective view of a prior art device.
Figure 7:
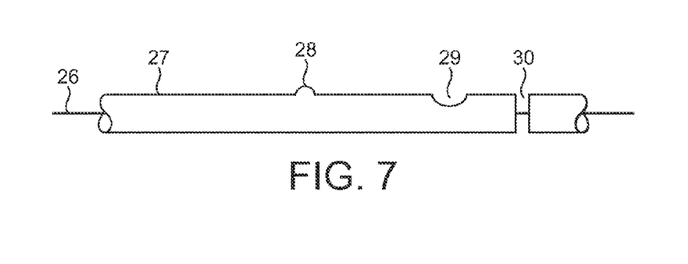
FIG. 7 is a right-side elevation view of a section of an electric cable formed in an extrusion process having surface faults.

In order to illustrate the advantages of the invention in more detail, reference is made to FIG. 6 and FIG. 7, whereby the invention will be compared with known prior art.

FIG. 6 shows a prior art system comprising a motor M driven multifaceted known polygonal mirrored scanning system G illuminated intermittently with a ray of light from source S. As obvious to one skilled in the arts, the scanning frequency of this system is limited by the rotational speed of the motor M and the number of facets on the mirrored polygon G receiving the beam of light from a light source S. In practice, a system using this principle could achieve up to 800 scans/sec.

By way of example of the operation of the prior art, FIG. 7 shows a section of an electric cable profile to be scanned whereby the metallic conductor 26 is insulated with plastic 30 material 27. The usual surface faults that may occur during manufacture are ridges 28, valleys 29 and bare patches 30, any one of which could be 2-3 mm in length. For example, let us assume that this cable was manufactured at a production speed of 1,200 meters/min, or 20,000 mm/sec, the distance between two successive scans, using the 800 scan system of FIG. 6, will be 20,000/800=25 mm. Therefore the illustrated prior art system is unlikely to detect any of the surface faults.

In other known prior art, an alternative non-scanning optical system exists, for checking surface integrity, which operates on the Shadow-Graph principle, by responding to changes in light intensity, thereby detecting surface imperfections. This system will detect the ridges, valleys and bare patches shown in FIG. 7 and provide a count of the number of the ridges, valleys and bare patches, but does not supply any other information.

By comparison, the system of the present invention as illustrated in FIG. 4B is capable of operating at a scanning frequency of 40,000 scans/sec. Therefore, considering the example in FIG. 5 of a production line running at a speed of 1,200 m/min or 20,000 mm/sec, the distance between two successive scans will be 20,000/40,000 mm, resulting in two scans per 0.5 mm of product length, providing far greater resolution than currently available techniques.

It is obvious from this example that the advantage of the present invention in an application of a product travelling at a high manufacturing speed is two-fold, firstly it provides a close coverage of the profile of the product, whereby it measures accurately the diameter or size of the product and secondly, follows closely the contour of the surface profile of the product, thereby locating any faults such as ridges valleys and the like, measuring the size of the faults and itemizing separately the number of each fault as it occurs along the length of the product.

Figure 8A:
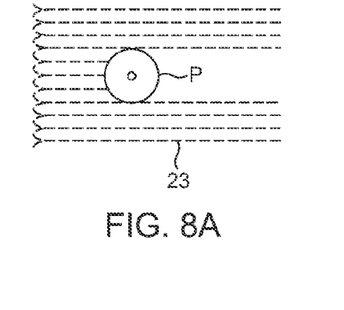
FIG. 8A is a front, elevation, cross-sectional view of a product being scanned by a curtain of rays, in accordance with embodiments of the present invention.
Figure 8B:
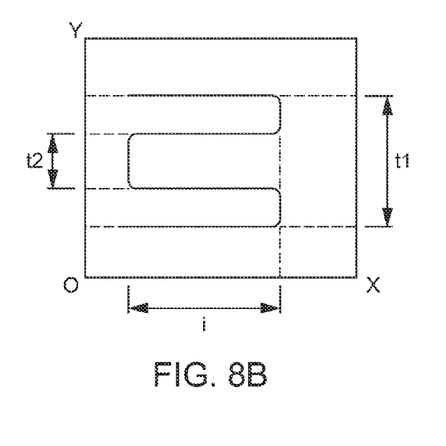
FIG. 8B is a graphical display of the spectral analysis of rays after scanning the product, in accordance with embodiments of the present invention.

The operation of the invention will now be explained in more detail. FIG. 8A shows a side view of product P, being scanned by a curtain sheet or rays 23 and with reference to FIG. 5, the resultant format of the rays after passing therethrough, are focused by lens 24 on to a photo sensor housed in unit 25. The photo sensor in unit 25 performs spectral analysis of the resultant rays and produces a waveform as shown in the graphical display of FIG. 8B, which follows accurately the path of the scanned rays as they travel across the product P. The X axis in FIG. 8B represents the light intensity (i) of the rays and the Y axis represents transit time (t1) of the rays across the aperture of lens 24. The dimensional and surface imperfections of the product P are derived by time related analysis of the time interval (t2) as depicted in FIG. 8B.

Figure 9:
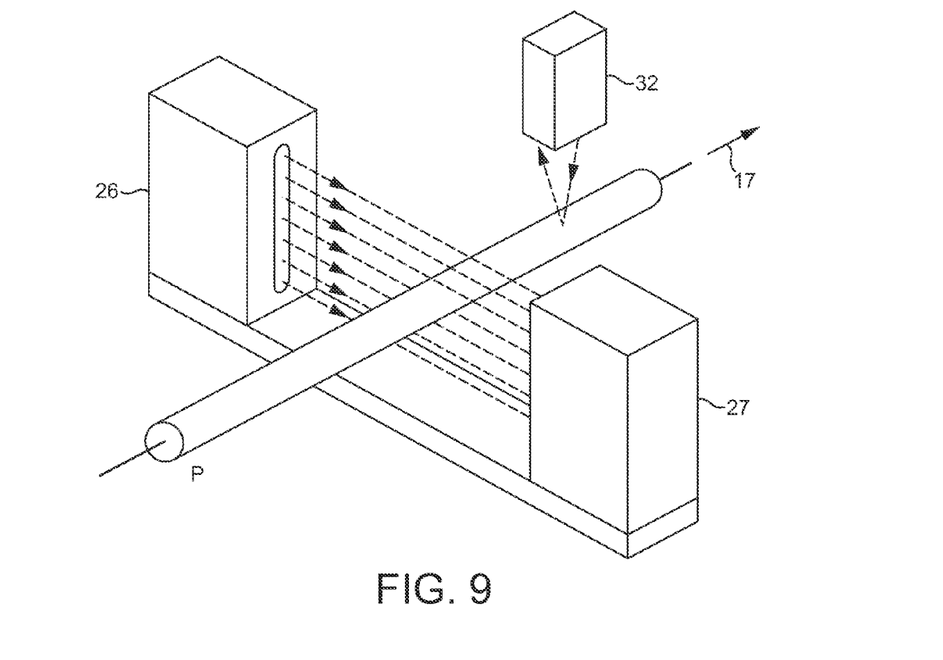
FIG. 9 is a top, front, left-side perspective view of a complete system for performing dimensional and surface integrity measurements on a travelling product, in accordance with embodiments of the present invention.

FIG. 9 illustrates a complete system for performing dimensional and surface integrity measurements on an electric cable P in its path of travel 17, comprising unit 26 housing items 18.1, 18.2, 20 and 22 and unit 27 housing items 24 and 25.

Figure 10:
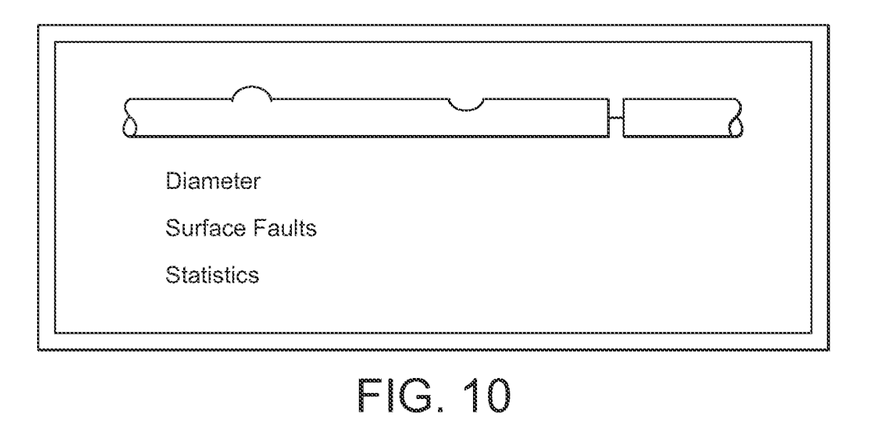
FIG. 10 is a front elevation view of a data logging station for displaying the diameter, surface faults and statistics resulting from the scanning of a product, in accordance with embodiments of the present invention.

In embodiments, unit 27 may output all measurement information by wireless communication such as Bluetooth or the like, to the Display and Data Logging Station shown in FIG. 10.

Figure 11:
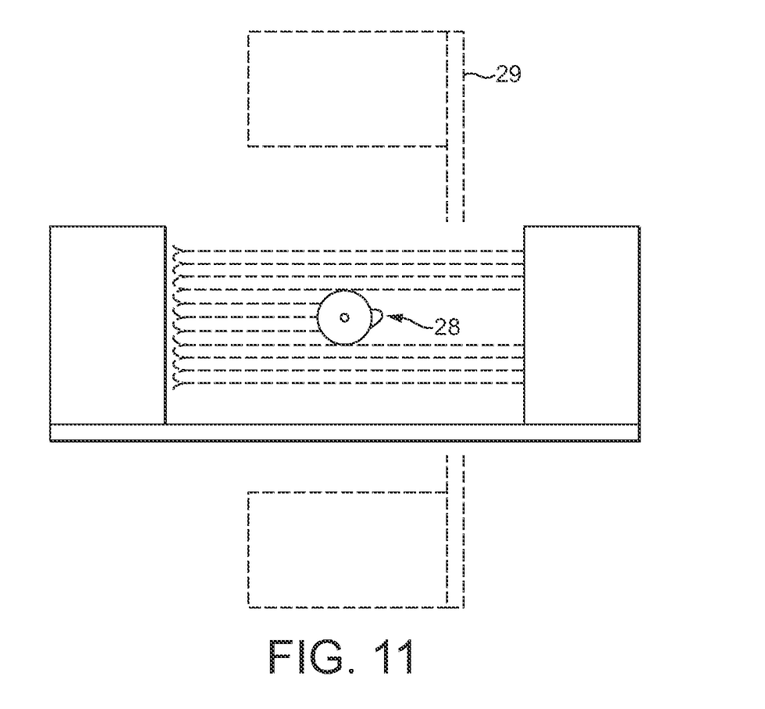
FIG. 11 is a front elevation view of a measuring system, a single plane profile system with reference to the scanning of a product, in accordance with embodiments of the present invention.

Now referring to FIG. 11, a front elevation view of an embodiment of the present invention is shown, which, up to this point we have considered as a "single plane", profile system. However it will be obvious to a person familiar with the arts, that some surface imperfections 28, as shown in FIG. 11, will be missed, as these would be on the "blind" side of the profile when using a single plane profile system. For this purpose a "two plane" profile system is disclosed 29 (shown dotted), to overcome this problem.

Figure 12:
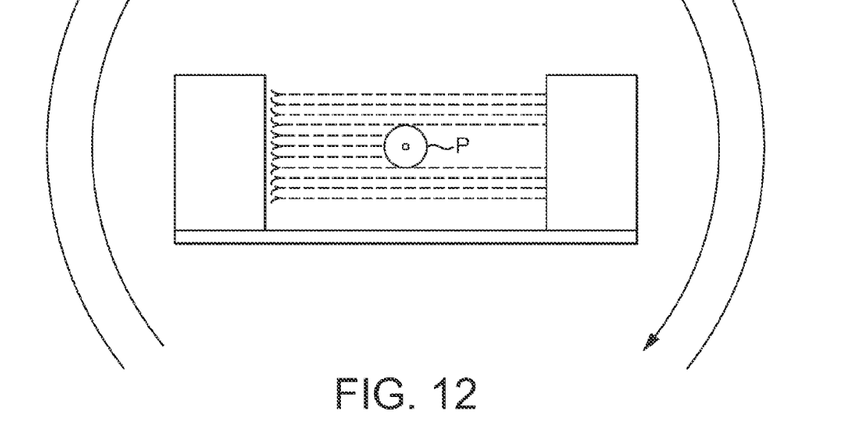
FIG. 12 is front elevation view of an alternative form of the system shown in FIG. 11 but capable of oscillatory motion about the product, in accordance with embodiments of the present invention.

In high quality product requirements, a "three plane" profile system (not shown) is recommended. As a more cost effective solution to overcome the all-round detection of surface imperfections, a "single plane" system may be used, as shown in FIG. 12, whereby oscillations occur in a "to and fro" motion 30 about the center of the travelling cable product P, or, alternatively, rotation may occur in a continuous motion 31 around the product P.

In order to further enhance the application usefulness of the present invention, a proprietary Laser Doppler non-contact speed/length Gauge 32, such as the Proton SL3060, as shown in FIG. 9 may be employed to provide accurate length information through the wireless transmission to the Data Logging Station as shown in FIG. 10.

Figure 13:
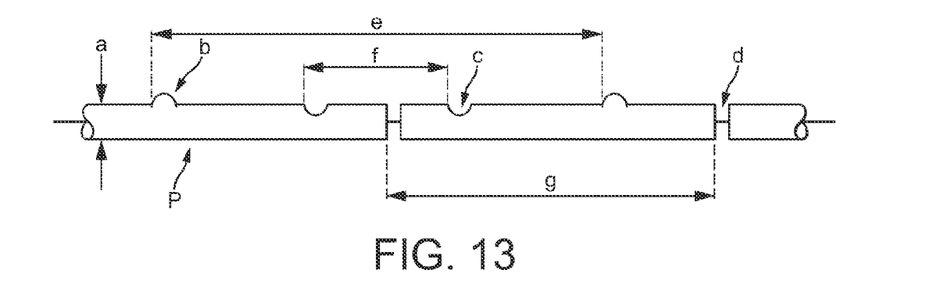
FIG. 13 is a right-side elevation view of the various imperfections detected by the various embodiments of the measuring system of the current disclosure for display on the data logging station shown in FIG. 10, in accordance with embodiments of the present invention.

Now referring to FIG. 13, an electric cable P is illustrated, whereby using the dimensional and surface measurements of unit 27 and the length information from the Proton Gauge 32, the following results may be obtained: instant/average product diameter; ridge size/length; valley size/length; length of bare patches; distance between successive ridges; distance between successive valleys; distance between bare patches; number of ridges per unit length; number of valleys per unit length; and the total number of ridges and valleys. The dimensional measurement and surface integrity results may be displayed on the screen of the Data Logging Station, as shown in FIG. 10, together with a continuously updating image of cable product P. A "freeze frame" facility may also be made available on the screen to allow periodic inspection of the progress of the product during manufacture.

When bare patches are detected, production may be automatically or manually stopped and the cable run scrapped. However, if the bare patches are detected near the end of a cable run, it may be possible to salvage part of the cable.

An additional advantage of this invention is that the manufacturer can use the available measurement and surface integrity information for statistical, as well as diagnostic purposes, whereby the frequency and location of specific faults can assist in finding which section of the production line, is the cause of the repetitive faults. The facility of data logging the dimensional and surface integrity information, as described in this disclosure, enables the manufacturer to set tolerance limits for the particular product under manufacture, whereby a certain amount of small size surface imperfections and/or diameter variations may be acceptable for the intended application and use of that product.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. An apparatus for scanning a product being manufactured in a continuous linear process comprising:
   two voltage generators for providing output frequencies of equal magnitude but of opposing phase;
   a magnetic foil with a mirrored face mounted for oscillation about a torsion axis, wherein the foil is magnetized to provide regions of opposite polarity thereon, respectively to each side of said torsion axis;
   an induction coil operatively associated with each of said voltage generators, each coil generating a magnetic force of alternating positive and negative polarity under the influence of said opposed phase output frequencies of the voltage generators, interacting respectively with said regions of opposite polarity thereby to provide a main magnetic driving force acting on one of said regions to oscillate the foil about the torsion axis and an opposing magnetic force acting on the other one of said regions to stabilize said oscillation and control an angular extent thereof;
   a light source for projecting a ray of light onto the mirrored face of the magnetic foil as the foil oscillates, thereby directing successive curtains of parallel rays across a product proceeding in a linear path of travel, wherein said successive curtains of parallel rays scan the product at the frequency of the generators; and
   an optical analysis device configured to analyze the format of the resulting light rays after their passage across the product, wherein such analysis provides dimensional measurements and verifies the product's surface integrity.

2. The apparatus as claimed in claim 1 wherein said light source is configured to direct a light ray onto the mirrored face of said oscillating magnetic foil, thereby creating a series of consecutive rays, and further comprising a first lens for receiving said consecutive rays wherein said first lens is configured to produce a curtain of parallel rays for scanning the product from one side thereof.

3. The apparatus as claimed in claim 2 further comprising a second lens configured to focus said rays, following their interception by said product, for analysis by said optical analysis device, wherein said optical analysis device is configured to determine the dimensional properties and surface integrity of the product.

4. The apparatus as claimed in claim 1 wherein said optical analysis device comprises a photo-sensor for performing spectral analysis of said rays focused thereon, thereby providing a measure of dimensional and surface imperfections of the product.

5. The apparatus as claimed in claim 1 wherein said light source is a laser.

6. The apparatus as claimed in claim 1 wherein said light source is a light emitting diode.

* * * * *

UNITED STATES PATENT AND TRADEMARK OFFICE
CERTIFICATE OF CORRECTION

PATENT NO. : 9,528,821 B2
APPLICATION NO. : 14/607437
DATED : December 27, 2016
INVENTOR(S) : John Kyriakis Page 1 of 1

It is certified that error appears in the above-identified patent and that said Letters Patent is hereby corrected as shown below:

On the Title Page

Item (73) Assignee should read:
Proton Products International Limited
10 Aylesbury End
Beaconsfield, Buckinghamshire
United Kingdom HP9 1LW Signed and Sealed this
Tenth Day of September, 2019

Andrei Iancu
*Director of the United States Patent and Trademark Office*